US008911769B2

(12) United States Patent
Spencer et al.

(10) Patent No.: US 8,911,769 B2
(45) Date of Patent: Dec. 16, 2014

(54) ORALLY DISINTEGRATING PHARMACEUTICAL COMPOSITION COMPRISING DICLOFENAC

(75) Inventors: Gavin Murray Spencer, Ruquefort les Pins (FR); Alexander Mark Schobel, Whitehouse Station, NJ (US); Greg Slominski, Elmwood, NE (US); Stephan Meyer, Genève (CH); Isabelle Rault, Segny (FR)

(73) Assignee: Novartis AG (CH)

( * ) Notice: Subject to any disclaimer, the term of this patent is extended or adjusted under 35 U.S.C. 154(b) by 1317 days.

(21) Appl. No.: 11/666,086

(22) PCT Filed: Oct. 20, 2005

(86) PCT No.: PCT/US2005/038090
§ 371 (c)(1),
(2), (4) Date: Apr. 20, 2007

(87) PCT Pub. No.: WO2006/047365
PCT Pub. Date: May 4, 2006

(65) Prior Publication Data
US 2008/0003267 A1 Jan. 3, 2008

Related U.S. Application Data

(60) Provisional application No. 60/620,706, filed on Oct. 21, 2004.

(51) Int. Cl.
*A61K 47/00* (2006.01)
*A61K 31/135* (2006.01)
*A61K 31/196* (2006.01)
*A61K 9/00* (2006.01)
*A61K 9/70* (2006.01)

(52) U.S. Cl.
CPC .............. *A61K 31/196* (2013.01); *A61K 9/0056* (2013.01); *A61K 9/006* (2013.01); *A61K 9/7007* (2013.01)

USPC .......... 424/439; 424/422; 424/434; 424/435; 424/441; 514/658; 514/646; 514/579

(58) Field of Classification Search
None
See application file for complete search history.

(56) References Cited

U.S. PATENT DOCUMENTS

| 4,765,983 | A | * | 8/1988 | Takayanagi et al. .......... 424/434 |
| 4,855,142 | A | | 8/1989 | Frankhauser et al. |
| 4,861,592 | A | | 8/1989 | Gottwald et al. |
| 5,256,699 | A | * | 10/1993 | Murphy et al. ................ 514/658 |
| 5,711,967 | A | * | 1/1998 | Juch .............................. 424/462 |
| 6,159,498 | A | | 12/2000 | Tapolsky et al. |
| 2003/0044446 | A1 | * | 3/2003 | Moro et al. .................... 424/426 |
| 2004/0202698 | A1 | * | 10/2004 | Ramji et al. ................... 424/443 |

FOREIGN PATENT DOCUMENTS

| CA | 2493881 | 5/2003 |
| WO | WO 96/18387 | 6/1996 |
| WO | WO 01/12161 | 2/2001 |
| WO | WO 03/101421 | 12/2003 |
| WO | WO2005/039543 | 5/2005 |

OTHER PUBLICATIONS

CRC Handbook of Food Additives, vol. 1, 2nd Ed. (1972), pp. 473-511.*
Database CA, Chemical Abstracts Service, Columbus, Ohio, US; Kurosaki, Yuji et al.: "Improvement of release rate of diclofenac from oro-muco-adhesive film dosage form by incorporating electrolytes and its effects on mucosal absorption" XP002370023 retrieved from STN. Database accession No. 1997:703675 abstract & Yakuzaigaku, 57 (3), 139-144 CODEN: YAKUA2: ISSN: 0372-7629. 1997.

* cited by examiner

*Primary Examiner* — Jeffrey T Palenik
(74) *Attorney, Agent, or Firm* — Gabriel Lopez; Diane E. Furman

(57) ABSTRACT

The invention relates to pharmaceutical compositions suitable for oral administration in the form of edible films comprising diclofenac.

37 Claims, No Drawings

ORALLY DISINTEGRATING PHARMACEUTICAL COMPOSITION COMPRISING DICLOFENAC

The invention relates to pharmaceutical compositions suitable to orally administer the well-known, widely used drug diclofenac. More specifically, it concerns edible films comprising diclofenac which rapidly and completely disintegrate in the mouth of a patient. Upon rapid disintegration of the edible films, diclofenac is released, easily swallowed and absorbed in the gastrointestinal tract in the usual way.

The concept of edible films comprising certain pharmaceutically active substances is well known in the art since long, see e.g. U.S. Pat. No. 4,136,162 (Fuchs and Hilmann, priority 1974). It is therefore remarkable that such oral dosage forms have hardly been commercialized during the last 30 years. One has to attribute this to the fact that a lot of technical and other obstacles, e.g. stability issues, had to cleared before one could think of commercializing a said product. At present, the most popular of these dosage forms on the market presumably is Listerine® PocketPaks® (USA), which is mainly intended as "breath freshener" and includes a mixture of menthol, eucalyptol, thymol and methyl salicylate, but none of the modern, highly efficacious drugs with a well defined, targeted mechanism of action.

It was a significant challenge to obtain suitable edible films comprising diclofenac according to the invention because quite a number of issues had to be accommodated: High bioavailability of diclofenac had to be ensured, the edible film had to be palatable to the patient and its stability, especially the chemical stability of the active substance within the edible film, had to be assured. Moreover, good organoleptic properties, such as an immediate softening of the film to prevent any adverse feeling in the mouth, and sufficient strength to allow for appropriate cutting and packaging operations, were required.

The inventors have overcome this challenge by providing diclofenac comprising edible films meeting said requirements.

Thus, the present invention relates to a pharmaceutical composition suitable for oral administration in the form of an edible film comprising diclofenac, which edible film completely disintegrates in the mouth of a patient in less than 60 seconds.

"Completely disintegrating" means that no macroscopic residue, e.g. a supporting insoluble layer, is left in the mouth of a patient. From a practical standpoint, the edible films of the invention completely dissolve in the mouth within the time periods indicated, with a proviso to be made from a strict scientific standpoint, namely that, obviously, components of the film that are not soluble in the saliva, like e.g. diclofenac free acid, will not dissolve but rather be dispersed and remain in the solid state.

Diclofenac is to be understood as including e.g. diclofenac free acid and pharmaceutically acceptable salts thereof, e.g. diclofenac sodium, diclofenac potassium or diclofenac epolamine. Diclofenac further includes e.g. resin complexes of diclofenac free acid and its pharmaceutically acceptable salts (also known as diclofenac resinates), e.g. the diclofenac sodium-cholestyramine complex or a diclofenac complex with polacrilin potassium (which is an Amberlite® resin). All these embodiments are referred to as "diclofenac" or "diclofenac components" respectively, in the following. Especially preferred are diclofenac free acid and diclofenac resinates, in particular diclofenac free acid.

Preferably, the edible films of the invention completely disintegrate in the mouth of a patient in less than 45 seconds, more preferably in less than 30 seconds, especially in less than 20 seconds and in particular in less than 15 seconds. Typically, they completely disintegrate within 1-60—preferably 2-45, more preferably 5-30 and in particular 5-20—seconds.

As the edible films of the invention completely disintegrate in the mouth so rapidly, adhesion of said films to the buccal mucosae does not play any significant role, and therefore said films may be either non-adhesive, slightly adhesive or adhesive to the buccal mucosa. Typically, they are non-adhesive or only slightly adhesive.

Edible films of the invention typically have a thickness of 3 mm or less, preferably of 1 mm or less, more preferably of 500 micrometers or less, and in particular of 100 micrometers or less. Thus, they typically have a thickness of from 10-3000—preferably 20-1000, more preferably 30-500 and in particular 40-100—micrometers.

Preferably, the edible films of the invention are mono-layer films which typically have a thickness of 500 micrometers or less, preferably of 250 micrometers or less, and more preferably of 100 micrometers or less. They typically have a thickness of from 10-500—preferably 20-250, more preferably 25-130, especially 30-100 and in particular 40-80—micrometers.

The edible films of the invention are not limited to any particular size, preferably they are rectangular, square or round, in particular rectangular or square, typically with an area of 2-20—preferably 2-12, more preferably 3-12 and especially 4-7, square centimeters, typically—if rectangular or square—with side lengths of 0.5-3 cm and 2-20 cm—preferably 1-3 cm and 2-5 cm —, respectively. A particularly preferred dimension is 2.2 cm×2.2 cm (square).

Typically, the edible films of the invention have a constant thickness and a uniformly homogeneous distribution of diclofenac.

Diclofenac is typically present in the film composition either in a dissolved or uniformly dispersed state.

The edible films of the invention typically comprise, apart from diclofenac, the following excipients: (A) at least one film forming polymer and (B) at least one plasticizer. Preferably, they comprise the following components: diclofenac, (A) at least one film forming polymer, (B) at least one plasticizer, and (C) at least one antioxidant. In another preferred embodiment, they comprise the following components: diclofenac, (A) at least one film forming polymer, (B) at least one plasticizer, (D) at least one flavor, (E) at least one sweetener, and—optionally—(C) at least one antioxidant.

As film forming polymers (A), there come into consideration, for example, cellulose derivatives, e.g. hydroxypropylmethyl cellulose (=hypromellose=HPMC), hydroxyethyl cellulose, hydroxypropyl cellulose, ethyl cellulose, hypromellose phthalate or cellulose phthalate; polyvinyl alcohol, sodium alginate, polyethylene glycol; natural gums, e.g. xanthane gum, tragacanth, guar gum, acacia gum or arabic gum; water-dispersible polyacrylates, e.g. polyacrylic acid, methacrylate copolymers or carboxyvinyl copolymers; polyvinylpyrrolidone, vinyl acetate/vinylpyrrolidone copolymers; modified starches, e.g. high amylose starch or hydroxypropylated high amylose starch; pullulan, amylose, dextrin, pectin, chitin, chitosan, levan, elsinan, collagen, gelatin, zein, gluten, soy protein isolate, whey protein isolate, casein; and mixtures thereof.

Preferred as film forming polymers (A) are hydroxypropylmethyl cellulose, hydroxyethyl cellulose, hydroxyethylmethyl cellulose, hydroxypropyl cellulose, hypromellose phthalate and mixtures thereof; and in particular hydroxypropylmethyl cellulose.

The film forming polymer (A) is typically present in amounts ranging from 5 to 90—preferably 10 to 80, more preferably from 20 to 80 and in particular from 20 to 70—weight-% of the final edible film (dry mass).

As plasticizers (B), there come into consideration, for example, polyalcohols, e.g. glycerol, polyethylene glycol, ethylene glycol or propylene glycol; glycerol monoesters with fatty acids, e.g. n-octanoic acid or oleic acid; sorbitol, polysorbate 80 [=polyoxyethylene (20) sorbitan monooleate], triethyl citrate, acetyl triethyl citrate, tributyl citrate or diethyl phthalate.

Preferred as plasticizers (B) are glycerol, polyethylene glycol, ethylene glycol, propylene glycol and mixtures thereof; and in particular glycerol.

The plasticizer (B) is typically present in amounts ranging from 0.1 to 15—preferably from 1 to 12, more preferably from 1 to 8 and even more preferably from 1.5 to 7—weight-% of the final edible film (dry mass). In a particular embodiment of the invention, the plasticizer (B) is glycerol and is present in amounts ranging from 1 to 12—preferably 1 to 7, and more preferably 1.5 to 6—weight-% of the film (dry mass).

Preferably, at least one antioxidant (C) is present in the composition of the edible films of the invention. Suitable antioxidants that can be included are those well known in the art, e.g. alpha-tocopherol, citric acid, butylated hydroxytoluene, butylated hydroxyanisole, ascorbic acid, fumaric acid, malic acid, sodium ascorbate or ascorbic acid palmitate. Moreover, it has been found that certain flavors (D), for example the grapefruit flavor 501508 A, the spearmint flavor 501495 T or the masking flavor 501483 T all mentioned below, can act as antioxidants (C), too.

In a particular embodiment of the invention, the edible films of the invention, especially those comprising diclofenac free acid, include at least one antioxidant (C) selected from the group consisting of alpha-tocopherol, ascorbic acid, citric acid and mixtures thereof.

Preferably, at least one flavor (D) is present in the composition of the edible films of the invention. The flavors that can be used include those known to the skilled artisan, such as natural, "natural-like" (=obtained by chemical synthesis but chemically identical to natural flavors) and artificial flavors. These flavors may be chosen e.g. from synthetic flavor oils, flavoring aromatics, oleo-resins and extracts derived e.g. from plants, leaves, flowers or fruits. Representative flavor oils include: spearmint oil, cinnamon oil, peppermint oil, clove oil, bay oil, thyme oil, cedar leaf oil, oil of nutmeg, oil of sage and oil of bitter almonds. Also useful are artificial, natural or synthetic fruit flavors such as vanilla, chocolate, coffee, cocoa and citrus oil, e.g. lemon, orange, grape, lime or grapefruit, and fruit essences, e.g. apple, pear, peach, strawberry, raspberry, cherry, plum, pineapple or apricot. Further commonly used flavors include mints such as peppermint (including menthol, especially levomenthol), artificial vanilla, cinnamon derivatives, and various fruit flavors, e.g. cherry or grape. Flavors such as aldehydes and esters, e.g. cinnamyl acetate, cinnamaldehyde, citral, diethylacetal, dihydrocarvyl acetate, eugenyl formate or p-methylanisole also come into consideration. Some further examples of aldehyde flavors are acetaldehyde; benzaldehyde; cinnamic aldehyde; citral, i.e. alpha-citral (geranial) and beta-citral (neral); decanal; ethyl vanillin; piperonal (heliotropine); vanillin; alpha-amyl cinnamaldehyde; butyraldehyde; valeraldehyde; citronellal; decanal; aldehyde C-8; aldehyde C-9; aldehyde C-12; 2-ethyl butyraldehyde; hexenal, i.e. trans-2; tolyl aldehyde; veratraldehyde; 2,6-dimethyl-5-heptenal (melonal); 2-6-dimethyloctanal; and 2-dodecenal. All flavors can be used either alone or in any desired combination thereof.

Preferred flavors (D), in liquid or solid form (powder), are grapefruit, peach, spearmint, strawberry, lime or masking flavors; menthol, sodium chloride; nucleotide compounds which contain a purine or pyrimidine group or derivative thereof which is bonded to a ribose or deoxyribose sugar moiety (see e.g. WO 2004/019885); and mixtures thereof. Advantageously, flavors (D) are combined with at least one sweetener (E), see below.

In one embodiment of the invention, the edible films of the invention, especially those comprising diclofenac free acid, include at least one flavor (D) selected from the group consisting of grapefruit—in particular grapefruit flavor 501508 A—, spearmint—in particular spearmint flavor 501495 T—, and masking flavor—in particular masking flavor 501483 T. All said flavors mentioned are available from Firmenich SA, CH-1217 Meyrin (Switzerland).

In another embodiment of the invention, the edible films of the invention, especially those comprising diclofenac free acid, include three flavors (D), namely a masking flavor, e.g. masking flavor 501483 T of Firmenich SA (CH), a grapefruit flavor, e.g. grapefruit flavor 501508 A of Firmenich SA (CH) and sodium chloride. Preferably, the latter combination of three flavors (D) is further combined with a sweetener (E) [see also below] selected from the group consisting of sucralose, acesulfame K, aspartame and any mixtures thereof—most preferably with acesulfame K. Advantageously, said latter combination of three flavors (D) with a sweetener (E) is further combined with an antioxidant (C) selected from the group consisting of alpha-tocopherol, ascorbic acid, citric acid, and mixtures thereof.

In another embodiment of the invention, the edible films of the invention, especially those comprising diclofenac free acid, include four flavors (D), namely a masking flavor, e.g. masking flavor 501483 T of Firmenich SA (CH), a spearmint flavor, e.g. spearmint flavor 501495 T of Firmenich SA (CH), sodium chloride and menthol. Preferably, the latter combination of four flavors (D) is further combined with a sweetener (E) selected from the group consisting of sucralose, acesulfame K, aspartame and any mixtures thereof—most preferably with acesulfame K. Advantageously, said latter combination of four flavors (D) with a sweetener (E) is further combined with an antioxidant (C) selected from the group consisting of alpha-tocopherol, ascorbic acid, citric acid, and mixtures thereof.

The amount of flavors employed is normally a matter of preference subject to such factors as flavor type, individual flavor, strength desired and need to taste-mask. Thus, the amount may be varied in order to obtain the result desired in the final product. Typically, amounts of 0.1 to 60, preferably 1 to 50, weight-% of flavors are used in the edible film (dry mass).

Preferably, at least one sweetener (E) is present in the composition of the edible films of the invention. Suitable sweeteners that can be included are those well known in the art, including both natural and artificial sweeteners. Suitable sweeteners include, for example, water-soluble sweetening agents such as monosaccharides, disaccharides and polysaccharides, e.g. xylose, ribose, glucose, mannose, galactose, fructose, sucrose, maltose, invert sugar, partially hydrolyzed starch, corn syrup solids, dihydrochalcones, monellin, steviosides or glycyrrhizin; water-soluble artificial sweeteners, e.g. saccharin in free acid form, soluble saccharin salts, e.g. sodium or calcium saccharin salts, cyclamate salts or acesulfame K; dipeptide based sweeteners, such as L-aspartic acid derived sweeteners, e.g. aspartame; water-soluble sweeteners derived from naturally occurring water-soluble sweeteners, e.g. sucralose; and protein based sweeteners, e.g. thaumatococcus danielli (Thaumatin I and II). Preferred as sweeteners (E) are sucralose, acesulfame K, aspartame and any mixtures thereof—in particular acesulfame K.

In general, an effective amount of sweetener (E) is utilized to provide the level of sweetness desired for a particular composition, and this amount will vary with the sweetener selected. This amount will typically be 0.01-10 weight-% of the edible film (dry mass).

Moreover, the edible films of the invention optionally include usual auxiliaries as known in the art, such as, for example, thickening agents, fillers, stabilizers, coloring agents, disintegration agents, solubilizing agents, preservatives or pH regulators.

Thickening agents are e.g. polyethylene oxide or methyl cellulose. Stabilizers are e.g. locust bean gum, alginic acid and derivatives, agar, carmellose (=carboxymethyl cellulose) and derivatives, croscarmellose (=cross-linked carboxymethyl cellulose) sodium. Fillers may be used e.g. to increase the total dry mass of a given edible film. The latter may be desirable for manufacture on an industrial scale, e.g. to adapt the formulation so that it can be properly processed by the converting equipment. Fillers can either be water-soluble, e.g. saccharose, glucose, fructose, maltose, maltitol, mannitol, xylitol or sorbitol, or water-insoluble, e.g. microcrystalline cellulose or titanium dioxide. Coloring agents, if present, are used in amounts effective to produce the desired color. Examples are titanium dioxide, or natural food colors and dyes suitable for food, drug and cosmetic applications, e.g. FD&C Blue No. 1 (=E133), FD&C Green No. 3, Fast green FCF, Chlorophyllis (=E140), Green S (=E142), Quinoline Yellow (=E104), Sunset yellow FCF (=E110). Disintegration agents are e.g. carmellose calcium and sodium (water dispersible), N-methyl-2-pyrrolidone, methylcellulose or sodium starch glycolate. Solubilizing agents are e.g. polyoxyethylene alkyl ethers, or cyclodextrines, e.g. of type alpha, beta or gamma. pH regulators are e.g. sodium carbonate or sodium hydrogen carbonate. Preservatives are e.g. parabens, benzoic acid, benzyl alcohol, chlorhexidine, sorbic acid or benzalkonium choride.

The edible films of the invention are advantageous inter alia because they greatly facilitate the administration of diclofenac to all who have potential problems with swallowing conventional oral dosage forms of diclofenac such as tablets or capsules, especially children and the elderly. Further, said edible films typically do release diclofenac rapidly and thus are beneficial when a quick pharmaceutical effect is desired. Moreover, they allow easy and discreet administration of the diclofenac in any circumstances, namely without the need to use water. This is ideal e.g. for traveling people who often do not have access to drinking water to swallow their medicine.

The dosages of diclofenac that can be incorporated into the edible films of the invention mainly depend on the final size of the film, and its thickness. Thus, by choosing a large area (e.g. up to 20 square centimeters) and/or a great thickness (e.g. between 250 and 500 micrometers or more) it is possible to load one edible film with up to 100 mg or more, e.g. with 10-100 mg and preferably 10-50 mg, of diclofenac.

Preferred, however, are edible films with an area of up to 12, e.g. 2-12 and especially 3-12, square centimeters and a thickness of 250 micrometers or less, more preferably 100 micrometers or less—e.g. of 20-250, and preferably of 30-100, micrometers. Those are typically loaded with 10-30 mg of diclofenac, e.g. an edible film of 4-6 square centimeters (e.g. 2.2 cm×2.2 cm or 2 cm×3 cm) with 12.5 mg, or one of 12 square centimeters (e.g. 2.5 cm×4.8 cm) with 30 mg of diclofenac.

Diclofenac is typically present in amounts ranging from 2 to 70—preferably from 5 to 60, more preferably from 10 to 50 and even more preferably from 20-50—weight-% of the final edible film (dry mass).

The inventors of the present invention have surprisingly found that the preferred diclofenac component to be used in the edible films as described above is diclofenac free acid. This is surprising, in particular, because diclofenac free acid, in contrast to e.g. diclofenac salts, is only poorly soluble in water and ethanol/water mixtures. Thus, it could be expected that several complications arising from its low solubility had to be dealt with. In particular, it appeared difficult to allow high loading (=doses) of diclofenac free acid and at the same time avoid agglomeration of the diclofenac free acid particles when only partially soluble in the solvent used for the manufacturing process. In other words, it looked challenging to assure and maintain the homogeneity of diclofenac free acid particles within the suspensions used to manufacture the edible films of the invention.

Surprisingly, it was found that said issues could be resolved by adapting the suspensions needed for manufacture to an optimal viscosity of 5000 to 13000 mPa·s (Brookfield viscosimeter, T=26° C., 50 rpm).

Another embodiment of the invention is characterized by edible films as described above which comprise diclofenac free acid with a mean particle size of 2 micrometers or less, preferably 1 micrometer or less. Those edible films exhibit high bioavailability of diclofenac (=good systemic delivery via the gastrointestinal tract) and have a palatable taste.

The beneficial properties of the compositions of the invention can be demonstrated e.g. by the following tests:

(a) Disintegration of the films: The disintegration time of the edible films is measured in vitro as well as in clinical tests in the mouth of patients. For example, the edible film of Example 2 completely disintegrates within 15 seconds.

(b) Plasma levels of diclofenac: The plasma levels of diclofenac are measured in vivo, e.g. in pigs, at different time intervals after oral administration of the edible films. Edible films according to the invention may produce similar plasma levels of diclofenac as a commercially available tablet comprising 12.5 mg diclofenac potassium (Voltaren® Dolo) [AUC (=Area Under the Curve) is essentially the same]. $T_{max}$ may be even shorter in edible films than in Voltaren® Dolo—what is desirable in many cases.

(c) Consumer testing of the organoleptic properties of the edible films: The perception of the edible films immediately after administration is tested. An immediate softening and pleasant feeling in the mouth are realized.

(d) Taste evaluation of the edible films: The taste of the edible films is evaluated in vitro with the aid of an "electronic tongue" equipment and also in consumer tests. For example, the taste of edible films of Examples 2-13 is found very palatable.

(e) Stability tests: The chemical and physical stability of the edible films is confirmed, e.g. in three months or one year studies under strictly controlled conditions (temperature/humidity).

(f) Non-aggregation of diclofenac free acid—non-micronized (mean particle size: 16 micrometers) or micronized—in dispersion: There was general concern that even when starting with material of low particle size (whether micronized or not), the latter might aggregate in dispersion during the manufacture of the edible films. Surprisingly, it is found that no such aggregation does occur in various solvents, e.g. water, water/ethanol or ethanol. For example, the particle size of—non-micronized or micronized—diclofenac free acid is measured with the aid of a Malvern (UK) laser particle size analyzer equipment before and after processing, under different conditions of manufacture, to an edible film. It is found that there essentially is no difference in the profile of the particle size distribution of diclofenac free acid as starting material and as it is released from edible films manufactured under different conditions (e.g. with ethanol, without ethanol, without ethanol but with homogenization) once disintegrated in water.

The edible films of the invention can be manufactured, for example, as follows: The diclofenac component, flavor, plasticizer, sweetener (and further excipients optionally being present) are added to a solvent or solvent mixture, e.g. water, water/ethanol or ethanol, and stirred. The film forming agent is added slowly under stirring until a uniform, opaque or transparent, viscous liquid is obtained. The latter is stored in a vessel, while slow stirring is continued, to eliminate any bubbles. (I) At laboratory scale: The viscous liquid is spread, as a layer of uniform thickness, e.g. on a plate and dried in an oven. The dried layer is cut into edible films of a defined size (e.g. 2 cm×3 cm rectangles), and the latter are packed e.g. individually in pouches. (II) At an industrial scale: The viscous liquid is spread, as a layer of uniform thickness, on a paper liner with a continuous coating line with oven. The dried layer is cut into edible films of a defined size (e.g. 2.2 cm×2.2 cm squares), and the latter are packed individually in pouches with a converting and packaging equipment.

During manufacture, care must be taken to obtain the optimal viscosity of the liquid mixture to spread to ensure a perfect diclofenac suspension and thus produce an edible film with a satisfying uniformity of content. As is known in the art, said viscosity is dependent on factors like the amount and type of solvent(s) used, the amounts and types of film forming polymers (A) and plasticizers (B) used and the way the suspension is processed.

In a special embodiment, the edible films of the invention are manufactured with the use of water as the sole solvent—that is to say the process is run without ethanol and any other organic solvents.

In another embodiment, the edible films of the invention are manufactured with the use of ethanol as the sole solvent—that is to say the process is run without water.

Diclofenac free acid with a mean particle size of 2 micrometers or less, preferably 1 micrometer or less, is obtained from diclofenac free acid with a normal mean particle size (ca. 5-20 micrometers) e.g. by micronization, milling, super critical fluid treatment or other techniques known to those skilled in the art.

Diclofenac free acid with a mean particle size of 2 micrometers or less, preferably 1 micrometer or less, is useful to be incorporated into oral dosage forms of diclofenac especially because it has a palatable taste and provides high bioavailability of diclofenac. This is of particular relevance for so-called "orally disintegrating tablets"—also known as fast-melt, quick-dissolving, mouth-dissolving or orodispersible tablets—, and edible films, but also for other oral dosage forms, such as normal tablets, chewable tablets, lozenges, softgels or capsules. Thus diclofenac free acid with a particle size of 2 micrometers or less, preferably 1 micrometer or less, forms another embodiment of the invention.

The following examples illustrate the invention.

EXAMPLE 1

Edible Film Containing 12.5 mg of Diclofenac Potassium (Manufactured in the Presence of Water and Ethanol)

| Ingredients | Amount (mg) |
| --- | --- |
| Diclofenac potassium | 12.50 |
| Metolose 60 SH 50, (=hydroxypropylmethyl cellulose, "HPMC") | 12.00 |
| Glycerol | 0.90 |
| Masking flavor 501483 T (Firmenich SA, CH) | 12.50 |
| Grapefruit flavor 501508 A (Firmenich SA, CH) | 4.00 |
| Sodium chloride | 4.00 |
| Sucralose | 4.00 |
| Total dry mass | 49.90 |
| Water | 60.00 |
| Ethanol 96% | 90.00 |
| Total wet mass | 199.90 |

Process: Diclofenac potassium, the two flavors, sodium chloride, glycerol and sucralose are all added to a mixture of water and ethanol, and the mixture is stirred. Hydroxypropylmethyl cellulose (=HPMC) is added slowly during stirring until a uniform, transparent, viscous liquid is obtained. The mixture is stored in a vacuum container, while slowly stirring, to eliminate the bubbles. Then the viscous liquid is spread, as a layer of uniform thickness, on a plate and dried in an oven. The dried layer is cut into edible films of a defined size (2 cm×3 cm rectangles), and the latter are packed individually in pouches. The diclofenac potassium films obtained are transparent and slightly yellow.

EXAMPLE 2

Edible Film Containing 11.08 mg of Diclofenac Free Acid (Manufactured in the Presence of Water and Ethanol)

| Ingredients | Amount (mg) |
| --- | --- |
| Diclofenac free acid | 11.08 |
| Metolose 60 SH 50 (HPMC) | 12.00 |
| Glycerol | 0.90 |
| Masking flavor 501483 T (Firmenich SA, CH) | 5.50 |
| Grapefruit flavor 501508 A (Firmenich SA, CH) | 4.00 |
| Sodium chloride | 1.05 |
| Sucralose | 1.05 |
| Total dry mass | 35.58 |
| Water | 60.00 |
| Ethanol 96% | 90.00 |
| Total wet mass | 185.58 |

Process: The edible film is manufactured analogous to that of Example 1. In this case, the viscous liquid obtained is not transparent but rather opaque. The diclofenac free acid films finally obtained are slightly yellow and have a thickness of 60 micrometers.

EXAMPLE 3

Edible Film Containing 11.08 mg of Diclofenac Free Acid (Manufactured in the Presence of Water but Without Ethanol)

| Ingredients | Amount (mg) |
|---|---|
| Diclofenac free acid | 11.08 |
| Metolose 60 SH 50 (HPMC) | 28.50 |
| Glycerol | 2.62 |
| Spearmint flavor 501495 T, (Firmenich SA, CH) | 1.50 |
| Sucralose | 0.39 |
| Total dry mass | 44.09 |
| Purified water | 300.00 |
| Total wet mass | 344.09 |

Process: The edible film is manufactured analogous to that of Example 2. In this case, diclofenac free acid, spearmint flavor, glycerol and sucralose are all added to water (alone) and stirred. The diclofenac free acid films finally obtained are white.

EXAMPLE 4

Edible Film Containing Diclofenac Resinate (Equivalent to 12.5 mg Diclofenac Potassium) (Manufactured in the Presence of Water and Ethanol)

| Ingredients | Amount (mg) |
|---|---|
| Diclofenac sodium-cholestyramine resinate (having a diclofenac content of 26.5%) | 41.81 |
| Metolose 60 SH 50 (HPMC) | 50.00 |
| Glycerol | 3.00 |
| Spearmint flavor 501495 T (Firmenich SA, CH) | 1.00 |
| Levomenthol | 1.00 |
| Sucralose | 0.50 |
| Total dry mass | 97.31 |
| Water | 150.00 |
| Ethanol 96% | 280.00 |
| Total wet mass | 527.31 |

Process: Levomenthol is dissolved in ethanol, and water is added to that solution. Diclofenac resinate, spearmint flavor, glycerol and sucralose are all added and the mixture is stirred. HPMC is added slowly during stirring until a uniform and viscous liquid is obtained. The mixture is stored in a vacuum container, while slowly stirring, to eliminate the bubbles. Then the viscous liquid is spread, as a layer of uniform thickness, on a plate and dried in an oven. The dried layer is cut into edible films of a defined size, and the latter are packed individually in pouches. The thickness of the diclofenac resinate films obtained is 200 micrometers, and said films are yellow.

EXAMPLE 5

Edible Film Containing 11.08 mg of Diclofenac Free Acid

| Ingredients | Amount (mg) |
|---|---|
| Diclofenac free acid | 11.08 |
| HPMC | 8.00 |
| Glycerol | 0.70 |
| Masking flavor 501483T (Firmenich SA, CH) | 2.75 |
| Spearmint flavor 501495 T (Firmenich SA, CH) | 0.70 |
| Sodium chloride | 0.75 |
| Levomenthol | 1.50 |
| Acesulfame K | 0.75 |
| Total dry mass | 26.23 |
| Water | 37.00 |
| Ethanol 96% | 59.00 |
| Total wet mass | 122.23 |

Process: Diclofenac free acid, the two flavors, levomenthol and glycerol are added to ethanol, and the mixture is stirred. Hydroxypropylmethyl cellulose (=HPMC) is added slowly during stirring until a white, uniform liquid is obtained. An aqueous solution of sodium chloride and acesulfame K is slowly added until a white, uniform and viscous liquid is obtained. The mixture is stored in a vacuum container, while slowly stirring, to eliminate the bubbles. Then the viscous liquid is spread, as a layer of uniform thickness, on a plate and dried in an oven. The dried layer is cut into edible films of a defined size (2 cm×3 cm rectangles), and the latter are packed individually in pouches. The diclofenac free acid films obtained are slightly yellow and have a thickness of 60 micrometers.

EXAMPLE 5A

This example is identical to Example 5, with the exception that the composition, in addition, includes 5 mg of microcrystalline cellulose and so has a total dry mass of 31.23 mg (instead of 26.23 mg in Example 5). During manufacture, the microcrystalline cellulose is added to the ethanolic mixture just after diclofenac free acid.

EXAMPLE 6

This example is identical to Example 5, with the exception that the composition, in addition, includes 0.005 mg of alpha-tocopherol, which is added just before the film forming polymer, HPMC. Thus, the total dry mass is 26.235 mg here.

EXAMPLE 7

Edible Film Containing 11.08 mg of Diclofenac Free Acid

| Ingredients | Amount (mg) |
|---|---|
| Diclofenac free acid | 11.08 |
| HPMC | 12.00 |
| Glycerol | 0.70 |

-continued

| Ingredients | Amount (mg) |
|---|---|
| Citric acid monohydrate | 3.00 |
| Spearmint flavor 501495 T (Firmenich SA, CH) | 0.70 |
| Sodium chloride | 0.75 |
| Levomenthol | 1.50 |
| Acesulfame K | 0.75 |
| Total dry mass | 30.48 |
| Water | 37.00 |
| Ethanol 96% | 59.00 |
| Total wet mass | 126.48 |

Process: The edible film is manufactured analogous to that of Example 5. In this case, no levomenthol is present and the citric acid monohydrate is dissolved in the aqueous solution, too.

EXAMPLE 8

Edible Film Containing 11.08 mg of Diclofenac Free Acid

| Ingredients | Amount (mg) |
|---|---|
| Diclofenac free acid | 11.08 |
| HPMC | 8.00 |
| Glycerol | 0.70 |
| Masking flavor 501483T (Firmenich SA, CH) | 2.75 |
| Grapefruit flavor 501508 A (Firmenich SA, CH) | 8.00 |
| Sodium chloride | 0.75 |
| Acesulfame K | 0.75 |
| Total dry mass | 32.03 |
| Water | 37.00 |
| Ethanol 96% | 59.00 |
| Total wet mass | 128.03 |

Process: The edible film is manufactured analogous to that of Example 5.

EXAMPLE 9

This example is identical with Example 8, with the exception that the composition, in addition, includes 0.005 mg of alpha-tocopherol, which is added just before the film forming polymer, HPMC. Thus, the total dry mass is 32.035 mg here.

EXAMPLE 10

This example is identical with Example 8, with the exception that the composition, in addition, includes 3.00 mg of citric acid monohydrate, which is dissolved in the aqueous solution, too. Thus, the total dry mass is 35.03 mg here.

EXAMPLE 11

Edible Film Containing 11.08 mg of Diclofenac Free Acid

| Ingredients | Amount (mg) |
|---|---|
| Diclofenac free acid | 11.08 |
| Methocel E5 (HPMC) | 3.20 |

-continued

| Ingredients | Amount (mg) |
|---|---|
| Methocel E50 (HPMC) | 4.80 |
| Glycerol | 0.70 |
| alpha-Tocopherol | 0.0064 |
| Spearmint flavor 501495 T (Firmenich SA, CH) | 0.70 |
| Masking flavor 501483 T (Firmenich SA, CH) | 2.75 |
| Sodium chloride | 0.75 |
| Levomenthol | 1.50 |
| Acesulfame K | 0.75 |
| Total dry mass | 26.24 |
| Water | 37.00 |
| Ethanol 96% | 28.00 |
| Total wet mass | 91.24 |

Process: The edible film is manufactured analogous to that of Example 6.

EXAMPLE 12

This example is identical with Example 11, with the exception that the composition, instead of 2.75 mg masking flavor 501483 T and 0.0064 mg alpha-tocopherol, includes 3.00 mg of citric acid monohydrate, which is dissolved in the aqueous solution, too. Thus, the total dry mass is 26.48 mg here.

EXAMPLE 13

Edible Film Containing 11.08 mg of Diclofenac Free Acid

| Ingredients | Amount (mg) |
|---|---|
| Diclofenac free acid | 11.08 |
| (A) Natrosol 250 HX (Hydroxyethylcellulose) | 6.00 |
| (B) Glycerol | 5.00 |
| (D) Spearmint flavor 501495 T (Firmenich SA, CH) | 0.70 |
| (D) Masking flavor 501483 T (Firmenich SA, CH) | 2.75 |
| (D) Sodium chloride | 0.75 |
| (D) Levomenthol | 1.50 |
| (E) Acesulfame K | 0.75 |
| Total dry mass | 28.53 |
| Water | 120.00 |
| Ethanol 96% | 110.00 |
| Total wet mass | 258.53 |

Process: The edible film is manufactured analogous to that of Example 5.

The invention claimed is:
1. An orally disintegrating pharmaceutical composition for administering diclofenac to a patient in need thereof for absorption in the gastrointestinal tract which consists essentially of an edible, mono-layer film, said mono-layer film having uniformly dispersed therein micronized diclofenac provided as the free acid, said mono-layer film comprising (A) at least one film forming polymer, (B) at least one plasticizer, (C) at least one antioxidant and (D) at least one flavor, and said mono-layer film being capable of completely disintegrating in the mouth of the patient within 60 seconds of administration.

2. A pharmaceutical composition according to claim 1, which has a thickness of 250 micrometers or less.

3. A pharmaceutical composition according to claim 1, wherein diclofenac is present in amounts ranging from 10 to 50 wt. %, (A) is present in amounts ranging from 10 to 80 wt. %, and (B) is present in amounts ranging from 1 to 10 wt. %, in each case of the final edible film (dry mass).

4. A pharmaceutical composition according to claim 1, wherein (A) is selected from the group consisting of hydroxypropylmethyl cellulose, hydroxyethyl cellulose, hydroxypropyl cellulose, cellulose phthalate, and mixtures thereof.

5. A pharmaceutical composition according to claim 1, wherein (A) is hydroxypropylmethyl cellulose.

6. A pharmaceutical composition according to claim 1, wherein (B) is selected from the group consisting of glycerol, polyethylene glycol, ethylene glycol, propylene glycol, and mixtures thereof.

7. A pharmaceutical composition according to claim 1, wherein (B) is glycerol.

8. A pharmaceutical composition according to claim 1, wherein (C) is selected from the group consisting of alpha-tocopherol, ascorbic acid, citric acid, and mixtures thereof.

9. A pharmaceutical composition according to claim 1, wherein (D) is selected from the group consisting of natural flavors, synthetic flavors, and artificial flavors.

10. A pharmaceutical composition according to claim 9, wherein (D) is selected from the group consisting of natural or synthetic flavor oils, flavoring aromatics, oleo-resins, extracts derived from plants, artificial, natural, or synthetic fruit flavors, aldehydes, esters, menthol, sodium chloride; nucleotide compounds which contain a purine or pyrimidine group or a derivative thereof which is bonded to a ribose or deoxyribose sugar moiety; and mixtures thereof.

11. A pharmaceutical composition according to claim 9, wherein (D) is selected from the group consisting of grapefruit, peach, spearmint, strawberry, and lime.

12. A pharmaceutical composition according to claim 9, wherein (D) is selected from the group consisting of grapefruit flavor, spearmint flavor, and masking flavor.

13. A pharmaceutical composition according to claim 9, wherein (D) is selected from the group consisting of spearmint oil, cinnamon oil, peppermint oil, clove oil, bay oil, thyme oil, cedar leaf oil, oil of nutmeg, oil of sage, oil of bitter almonds, vanilla, chocolate, coffee, cocoa, lemon, orange, grape, lime, grapefruit, apple, pear, peach, strawberry, raspberry, cherry, plum, pineapple, apricot, peppermint, menthol, levomenthol, artificial vanilla, cinnamyl acetate, cinnamaldehyde, citral, diethylacetal, dihydrocarvyl acetate, eugenyl formate, p-methylanisole, acetaldehyde, benzaldehyde, alpha-citral, beta-citral, decanal, ethyl vanillin, piperonal, vanillin, alpha-amyl cinnamaldehyde, butyraldehyde, valeraldehyde, citronellal, decanal, aldehyde C-8, aldehyde C-9, aldehyde C-12, 2-ethyl butyraldehyde, hexenal, tolyl aldehydes, veratraldehyde, 2,6-dimethyl-5-heptenal, 2-6-dimethyloctanal, and 2-dodecenal.

14. A pharmaceutical composition according to claim 9, wherein (D) is selected from the group consisting of masking flavor, a grapefruit flavor, and sodium chloride.

15. A pharmaceutical composition according to claim 9, wherein (D) is selected from the group consisting of masking flavor, a spearmint flavor, sodium chloride, and menthol.

16. A pharmaceutical composition according to claim 1, which comprises at least one sweetener (E) selected from the group consisting of sucralose, acesulfame K, aspartame, and any mixtures thereof.

17. A pharmaceutical composition according to claim 1, wherein (C) comprises ascorbic acid.

18. A pharmaceutical composition according to claim 1, wherein (A) comprises hydroxypropylmethyl cellulose, (B) comprises polyethylene glycol, and (C) comprises ascorbic acid.

19. A pharmaceutical composition according to claim 18, wherein (D) comprises spearmint flavor.

20. A pharmaceutical composition according to claim 18, wherein (D) comprises spearmint flavor and menthol.

21. A pharmaceutical composition according to claim 20, which additionally comprises at least one sweetener (E) selected from the group consisting of sucralose, acesulfame K, aspartame, and any mixtures thereof.

22. A pharmaceutical composition according to claim 1, wherein
(A) is selected from the group consisting of hydroxypropylmethyl cellulose, hydroxyethyl cellulose, hydroxypropyl cellulose, cellulose phthalate, and mixtures thereof.
(B) is selected from the group consisting of glycerol, polyethylene glycol, ethylene glycol, propylene glycol, and mixtures thereof; and
(C) is selected from the group consisting of alpha4ocopherol, ascorbic acid, citric acid, and mixtures thereof.

23. A pharmaceutical composition according to claim 22, wherein (A) comprises hydroxypropylmethyl cellulose and (B) comprises glycerol.

24. A pharmaceutical composition according to claim 22, wherein (A) comprises hydroxypropylmethyl cellulose and (B) comprises polyethylene glycol.

25. A pharmaceutical composition according to claim 22, wherein (C) comprises ascorbic acid.

26. A pharmaceutical composition according to claim 23, wherein (C) comprises citric acid.

27. A pharmaceutical composition according to claim 23, wherein (C) comprises alphatocopherol.

28. A pharmaceutical composition according to claim 22, having a thickness of from 10-500 microns.

29. A pharmaceutical composition according to claim 22, having a thickness of from 20-250 microns.

30. A pharmaceutical composition according to claim 24, having a thickness of 25-130 microns.

31. A pharmaceutical composition according to claim 1, wherein the micronized diclofenac has a mean particle size of 2 micrometers or less.

32. A pharmaceutical composition according to claim 1, wherein the micronized diclofenac has a mean particle size of 1 micrometer or less.

33. A pharmaceutical composition according to claim 22, wherein the micronized diclofenac has a mean particle size of 1 micrometer or less.

34. A pharmaceutical composition according to claim 1, comprising diclofenac free acid in the amount of 11.08 mg.

35. A pharmaceutical composition according to claim 22, comprising diclofenac free acid in the amount of 11.08 mg.

36. A pharmaceutical composition according to claim 34, having an area of 3-12 square centimeters and a thickness of 20-250 micrometers.

37. A pharmaceutical composition according to claim 35, having an area of 4-5 square centimeters and a thickness of 25-130 micrometers.

* * * * *